(12) United States Patent
Wood et al.

(10) Patent No.: US 7,931,957 B2
(45) Date of Patent: *Apr. 26, 2011

(54) FIBER MATERIAL HAVING IMPROVED MALODOR SCAVENGER PROPERTIES

(75) Inventors: Will Wood, Arden Hills, MN (US); Neil Beaverson, Vadnais Heights, MN (US)

(73) Assignee: Cellresin Technologies, LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/275,409

(22) Filed: Nov. 21, 2008

(65) Prior Publication Data

US 2009/0075064 A1 Mar. 19, 2009

Related U.S. Application Data

(63) Continuation of application No. 10/656,670, filed on Sep. 5, 2003, now Pat. No. 7,470,464.

(51) Int. Cl.
*B32B 27/04* (2006.01)
(52) U.S. Cl. .................. 428/296.7; 264/465; 604/358
(58) Field of Classification Search ............... 428/296.7; 604/358

See application file for complete search history.

(56) References Cited

U.S. PATENT DOCUMENTS 5,429,628 A * 7/1995 Trinh et al. .................. 604/359
7,470,464 B2 * 12/2008 Wood et al. ................ 428/296.7

FOREIGN PATENT DOCUMENTS

| CN | 2100898 | 4/1992 |
|----|---------|--------|
| JP | 55-115440 | 9/1980 |
| JP | 1991-14678 | * 1/1991 |
| JP | 2003-166156 | 6/2003 |
| JP | 06 287355 | 10/2006 |
| WO | 96/00260 | 1/1996 |
| WO | 03 016148 | 2/2003 |
| WO | 03 025067 | 3/2003 |

OTHER PUBLICATIONS

Rendlean, Jr., "*Enhancement of cyclodextrin production through use of debranching enzymes*", Biotechnical. Appln. Biochem., vol. 26, 1997, pp. 51-61.
Hedges, : "*Cyclodetrin: Production, Properties, and Applications*", VCH, New York, 1992, pp. 319-333.

* cited by examiner

*Primary Examiner* — Lynda Salvatore
(74) *Attorney, Agent, or Firm* — Fay Kaplun & Marcin, LLP

(57) ABSTRACT

Described are fiber materials having improved malodor scavenger properties and a process for the manufacture of said materials. In particular, described are fiber materials usable in the manufacture of disposable or washable diapers, incontinent products, sanitary napkins and other such hygiene and personal care articles with improved malodor scavenger properties, and to methods of manufacturing such materials. It has been found that the incorporation of, especially nano-sized, metal particles and/or a cyclodextrin material into fibers creates a "reactive" material having excellent malodor scavenging properties. More specifically, it has been found that the presence of nanosized metal or metal alloy particles and/or a cyclodextrin material in a fiber material, preferably a synthetic polymer material and more preferably a synthetic thermoplastic polymer fiber material leads to fiber materials or nonwovens having odor-controlling properties. The fiber material especially is useful in the manufacture of hygienic products like disposable diapers.

11 Claims, 3 Drawing Sheets

FIBER MATERIAL HAVING IMPROVED MALODOR SCAVENGER PROPERTIES

PRIORITY CLAIM

This application is a Continuation application of U.S. patent application Ser. No. 10/656,670 filed on Sep. 5, 2003, now U.S. Pat. No. 7,470,464 entitled "Fiber Material Having improved Malodor Scavenger Properties". The entire disclosure of the prior application is considered as being part of the disclosure of the accompanying application and hereby expressly incorporated by reference herein.

FIELD OF THE INVENTION

The invention relates to fiber materials having improved malodor scavenger properties and a process for the manufacture of said materials. The invention especially relates to fiber materials usable in the manufacture of disposable or washable diapers, incontinent products, sanitary napkins and other such hygiene and personal care articles with improved malodor scavenger properties, and to methods of manufacturing such materials.

The present invention also relates to corresponding articles, and methods of manufacturing such articles.

BACKGROUND INFORMATION

Besides having some liquid-impermeable barrier film or sheet, hygiene and personal care articles such as diapers, incontinent products and sanitary napkins are often provided with some absorptive capacity for more efficiently containing the liquid or semi-liquid excretions which they are intended to prevent from soiling underwear or other items of clothing.

Even when the article is disposable, malodors caused by volatile components or volatile decomposition products of such excretions can cause discomfort, already during normal wear before the article is disposed.

A related problem arises in the temporary storage of such soiled articles, be they disposable or washable, before their disposal or before laundering, as applicable. Malodors emanating from such stored articles are highly undesirable.

A permeant, contaminant or volatile in the meaning of the present invention is a substance that can exist in the atmosphere at a substantial detectable concentration and can escape from such an article. A large variety of such permeants or volatiles are known.

Usually soiled diapers are stored in a lockable container or resealable garbage bag, which is e.g. placed in the nursery, before transporting them to an outdoor storage vessel. It is widespread to use plastic diaper pails having a tight lid for the temporary storage of the soiled diapers. Said bags or diaper pails reduce the release of the unpleasant odors when sealed. However, the barrier properties of e.g. thermoplastic garbage bags known in the art are limited and are not satisfactory.

In our co-pending application WO 03/025067 entitled "Barrier material having nanosized metal particles" we have disclosed an improved barrier film or sheet material that can e.g. be used to produce improved containers and improved constructive components for articles such as diapers.

While we will hereinafter disclose and exemplify the invention with reference to specific embodiments and applications such as diapers, it is to be understood that this disclosure applies mutatis mutandis to all other comparable articles suffering from similar malodor problems.

Disposable diapers have met with increased commercial acceptance in recent years and many different constructions have been proposed and used. Usually, the moisture absorbing functions are accomplished by a multilayer diaper comprising a liquid pervious top sheet or facing layer, intended to be facing the wearer during use, in the form of a nonwoven material for example a spunbond material. Moreover, disposable diapers often have a liquid acquisition layer between the topsheet and the absorbent body, said liquid acquisition layer having the ability to quickly receive large amounts of liquid, to distribute it and temporarily store it before it is absorbed by the underlying absorbent body. This is important especially in today's thin compressed absorbent bodies often with a high amount of so called superabsorbents, which have a high absorption capacity but in many cases a too low absorption speed in order to be able to absorb the large amount of liquid that can be discharged. The top sheet or facing layer often is made of a porous material and its fibers have less wettability for water than the fibers of the absorbing material, resulting in a tendency for liquid to flow from the facing layer into the absorbing unit. Liquid, which might pass through the absorbing unit during discharge, (when flow is rapid) is held back by an impervious backing sheet or film for sufficient time to permit absorption to take place. However, the outer or backing layer does not prevent volatile substances or odors from permeating through said layer.

The absorbent body can be of any conventional kind. Examples of common absorption materials are cellulosic fluff pulp, tissue layers, highly absorbent polymers (so called superabsorbents), absorbent foam materials, absorbent nonwoven materials and the like. It is known to combine cellulosic fluff pulp with other materials in an absorbent body. It is also common to have absorbent bodies comprising layers of different materials with different properties concerning liquid acquisition capacity, liquid distribution capacity and liquid storage capacity. Conventional absorbent layers or bodies have no odor-controlling properties.

Many of the materials used in the manufacture of the aforementioned sanitary products are fibrous materials. Beside cellulosic fiber materials, materials derived from synthetic or thermoplastic fibers are useful for a wide variety of applications in diapers, feminine hygiene products, incontinence products, towels, medical garments, medical and pharmaceutical products and many others.

It is clear that the problems indicated above with respect to soiled diapers apply to the same extent to other articles, e.g. incontinent products, medical dressings, sanitary napkins or any other article emitting volatile substances.

While some of the malodor problems caused by such soiled hygiene and personal care articles can be overcome by the improvements disclosed in our said co-pending application, it is possible to further improve such articles, in terms of their olfactory properties both in use and in storage after use, by a different approach based on our present invention, as disclosed herein.

In WO 97/33044 the use of cyclodextrin in rigid or semi-rigid cellulosic sheets is disclosed. The cyclodextrin acts as a barrier or a trap for contaminants. The barrier properties of the material disclosed in WO 97/33044 are based on entrapment of the respective permeants in the internal hydrophobic space of the cyclodextrin molecule. The cyclodextrin material is generally used in the form of a compatible, derivatized cyclodextrin. According to WO 97/33044 the preferred cyclodextrin is a derivatized cyclodextrin having at least one substituent group bonded to the cyclodextrin molecule.

Moreover, it is known from WO 97/30122 that the barrier properties of a thermoplastic polymer can be improved by forming a barrier layer with a dispersed compatible cyclodextrin derivative in the polymer.

WO 93/10174 is directed to thermoplastic films containing one or more metal powders selected from aluminum powder, magnesium powder, zinc powder and manganese powder.

The application is directed to a thermoplastic film which is characterized in that the film comprises at least 0.1 wt. %, preferably 0.5 to 6 wt. %, based on the total weight of the mixture of thermoplastic and filler, of at least one metal powder, selected from the group consisting of aluminum powder, magnesium powder, manganese powder and mixtures thereof. According to WO 93/10174 the average particle size of the metal powders is in the range of 5-20 µm.

SUMMARY OF THE INVENTION

In none of the aforementioned documents of the prior art, fiber materials comprising fibers and dispersed in the fibers reactive metal particles and/or modified cyclodextrin, or articles made from such fibers are disclosed.

According to an exemplary embodiment of the present invention a fiber material is provided, the material comprising:
 (a) fibers; and
 (b) dispersed in the fibers, an effective malodor scavenging amount of particles of zinc or similar reacting metal or metal alloy, or a cyclodextrin material; wherein the cyclodextrin is free of an inclusion complex compound and the cyclodextrin comprises an α-cyclodextrin, a β-cyclodextrin, a γ-cyclodextrin or mixtures thereof, having pendant moieties or substituents that render the cyclodextrin compatible with the fiber material or
 a combination of said particles and said cyclodextrin material.

It is believed that the material according to this exemplary embodiment of the present invention has improved malodor scavenging properties.

DETAILED DESCRIPTION

Figure 1:
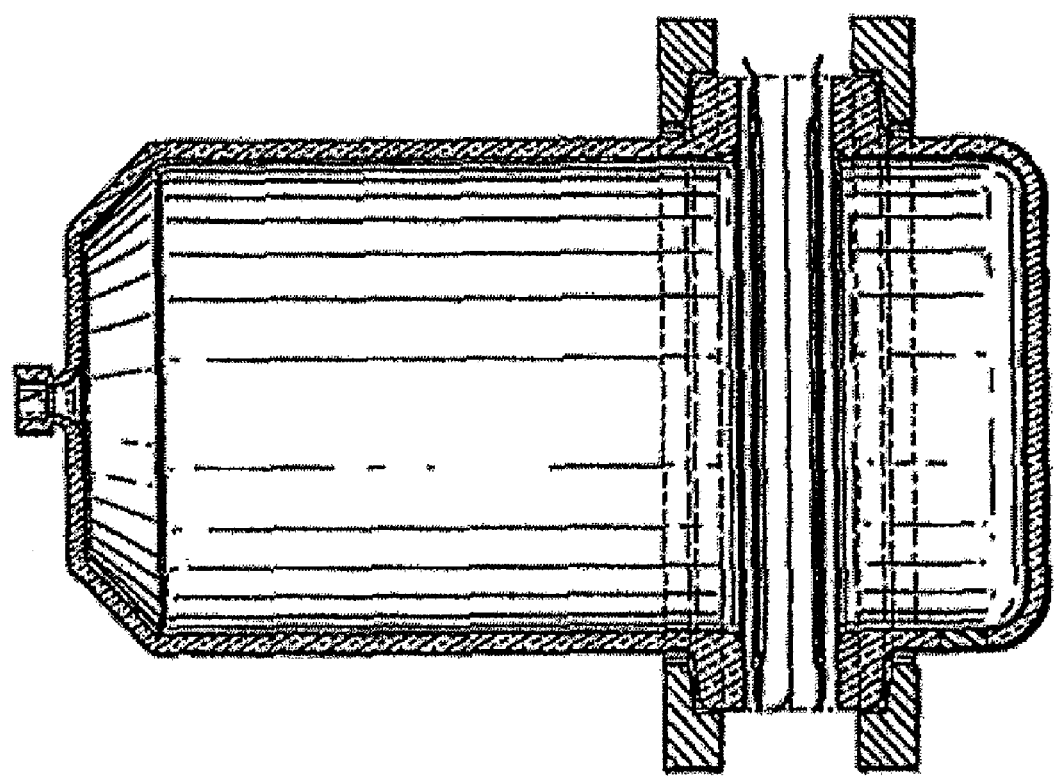
FIG. 1 Closed-Volume jar with aluminum sealing rings for use in fiber sorption tests.

Surprisingly, it has now been found that the incorporation of, especially nanosized, metal particles and/or a cyclodextrin material into fibers creates a "reactive" material which may have excellent malodor scavenging properties. More specifically, it is believed that the presence of nanosized metal or metal alloy particles and/or a cyclodextrin material in a fiber material, preferably a synthetic polymer material or a synthetic thermoplastic polymer fiber material may be advantageous in achieving excellent malodor scavenging properties.

In one important aspect of this invention, the fiber material used as absorbent and/or as constructive material in a hygiene or personal care article, comprises a cyclodextrin material or metal particles or a combination of cyclodextrin material and metal particles, capable of scavenging malodor-causing volatiles and permeants, said scavenging causing the complete or at least partial neutralization of said volatiles and permeants.

In another important aspect of the invention, such metal particles and/or cyclodextrin materials are comprised inside of the said fibers. In another aspect of the invention, said metal particles and/or cyclodextrin materials are dispersed throughout said fibers. In yet another aspect of this invention, the said metal particles are nanosized particles.

The invention includes a method of producing such fibers, which comprises incorporating such metal particles and/or cyclodextrin materials in the fibers when the fibers are produced.

The invention also includes articles made using such fibers e.g. in liquid-permeable layers and sheets such as top sheets in e.g. diapers, napkins and pads, and/or in liquid-absorbing layers or regions of e.g. diapers, napkins and pads.

The invention includes methods for manufacturing such articles, comprising the incorporation of such absorbing materials and/or sheet materials.

The metal particles in the meaning of the present invention may be "nanosized particles" having an average diameter generally in the range of 10 to 500 nm, or in the range of 40 to 250 nm or even in the range of 60 to 150 nm. It is believed in the present invention that the use of particles having an average diameter of more than 1000 nm may be disadvantageous, where the fiber thickness is reduced. Of course, where the fiber thickness is sufficient to incorporate bigger particles, the metal particles may be bigger than nanosized, as above defined. Additionally, larger metal particles may impact on fiber color (i.e. a darker color) a negative aspect in many personal care applications.

According to the present invention it may be advantageous to use zinc particles i.e. particles substantially consisting of metallic zinc, in unreacted form. However, also the use of similar reacting metal or metal alloy particles instead of, or in addition to, zinc particles is contemplated in the present invention. It may be advantageous that the zinc or other metal particles are essentially free of corresponding oxides.

If a cyclodextrin material is dispersed in the inventive fiber material, it should have some low moisture content, preferably a moisture content of about 1 wt.-%, based on the cyclodextrin material.

It has been found in the present invention that the inventive fiber materials containing metal particles and/or cyclodextrin derivatives are particularly suitable for the manufacture of diapers, incontinent products, medical dressings, sanitary napkins etc., since the fiber material functions as an effective scavenger of malodorous permeants, especially reactive permeants, emitting from excrements etc.

Volatiles or permeants emitting from e.g. excrements comprise low molecular organic acids, organic sulfides and thiols, amines, ammonia and aromatic alcohols. Most of these compounds have human sensory thresholds in the low parts per billion.

The inventive fiber materials are able to at least partly permanently scavenge the permeants reaching the fibers. In the context of this invention, "scavenging" comprises destructive as well as non-destructive neutralization or bonding of malodorous volatiles. Scavenging may e.g. involve chemical reaction with volatile molecules which leads to changes in their chemical characteristics or just bonding, complexing, chelating or other processes which fix the volatile molecules, more or less permanently, at or in the fibers without permanently changing the molecular structure of the volatiles.

Without wishing to be bound by any scientific theory, we assume that the metal-reactive permeants (e.g., volatile acids, sulfides, thiols, mercaptanes) react with the metal particles. The resulting reaction products in most cases have less odor. Moreover, the metal-reactive permeants, nonreactive permeants as well as the aforementioned reaction products are at least partly complexed by the cyclodextrin material, preventing their release into the environment. Accordingly, the incorporation or dispersion of cyclodextrin, metal particles or both into fibers may lead to a significant reduction of malodorous volatiles.

The polymer material of the fibers according to the present invention can be a thermoplastic material or a crosslinkable thermoplastic materials including polymers made from monomers including ethylene, propylene, butylene, butadiene, styrene and others. Moreover, such thermoplastic polymeric materials include poly(acrylonitrile-co-butadiene-co-styrene) polymers, acrylic polymers such as the polymethylmethacrylate, poly-n-butyl acrylate, poly(ethylene-co-acrylic acid), poly(ethylene-co-methacrylate), etc.; cellophane, cellulosics including cellulose acetate, cellulose acetate propionate, cellulose acetate butyrate and cellulose triacetate, etc.; fluoropolymers including polytetrafluoroethylene (Teflon®), poly(ethylene-co-tetrafluoroethylene) copolymers, (tetrafluoroethylene-co-propylene) copolymers, polyvinyl fluoride polymers, etc., polyamides such as nylon 6, nylon 6,6, etc.; polycarbonates; polyesters such as poly(ethylene-co-terephthalate), poly(ethylene-co-1,4-naphthalene dicarboxylate), poly(butylene-co-terephthalate); polyimide materials; polyethylene materials including low density polyethylene; linear low density polyethylene, high density polyethylene, high molecular weight high density polyethylene, etc.; polypropylene, biaxially oriented polypropylene; polystyrene, biaxially oriented polystyrene; vinyl films including polyvinyl chloride, (vinyl chloride-co-vinyl acetate) copolymers, polyvinylidene chloride, polyvinyl alcohol, (vinyl chloride-co-vinylidene dichloride) copolymers, specialty films including polysulfone, polyphenylene sulfide, polyphenylene oxide, liquid crystal polyesters, polyether ketones, polyvinylbutyral etc.

In an exemplary embodiment of the present invention the polymer material is a thermoplastic material such as PET (polyethylene terephthalate), PP (polypropylene) and PE (polyethylene) as conventionally used for fibers in hygiene and personal care article absorbents, top-sheets and other textile or non-woven components. It may be especially advantageous to use polypropylene as the polymer material.

The inventive fiber material or the fibers may be in the form of a non-woven material containing spunbound, conjugate and bi-constituent fibers comprising said metal particles and/or cyclodextrin material. A nonwoven fabric or web is a web having a structure of individual fibers or threads which are held or bound together. Nonwoven fabrics or webs have been formed from many processes such as for example, meltblowing processes, spunbonding processes, electrospinning and bonded carded web processes.

So-called "meltblown fibers" are fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers.

Meltblown fibers can be incorporated into a variety of nonwoven fabrics including composite laminates such as spunbond-meltblown-spunbond ("SMS") composite sheets. In SMS composites, the exterior layers are spunbond fiber layers that contribute strength to the overall composite, while the core layer is a meltblown fiber layer that provides barrier properties.

"Spunbonded fibers" refers to small diameter fibers which are formed by extruding molten thermoplastic material as filaments from a plurality of fine openings, which are usually circular capillaries of a spinnerette. The polymer is fiberized as it passes through fine openings arranged in one or more rows in the spinnerette, forming a curtain of filaments. The filaments are usually quenched with air at a low pressure, drawn, usually pneumatically and deposited on a moving foraminous mat, belt or forming wire to form the nonwoven fabric. Polymers useful in the spunbond process generally have a process melt temperature of between about 200° C. to 320° C.

The fibers produced in the spunbond process are generally in the range of from about 10 to about 100 µm in diameter, depending on process conditions and the desired end use for the materials to be produced from such fibers. For example, increasing the polymer molecular weight or decreasing the processing temperature result in larger diameter fibers.

So-called "nanofibers" are fibers formed by electrospinning processes. Nanofibers or nanofiber nonwoven webs usually have fibers in the range of from about 0.04 to about 2 µm in diameter. Nonwoven nanofiber materials are used in the manufacture of e.g. medical and pharmaceutical products, barrier fabrics and air filters.

Electrospinning uses an electric field to draw a polymer melt or polymer solution from the tip of a capillary to a collector. A voltage is applied to the polymer, which causes a jet of the polymer to be drawn toward a grounded collector. The fine jet forms polymeric fibers, Which are collected on a web.

The metal particles and/or the cyclodextrin material which provide the scavenging effect are generally incorporated in the fibers. It may be advantageous that the metal particles and/or the cyclodextrin material is uniformly dispersed in the fibers.

In the invention the amount of zinc or similar scavenging metal or metal alloy in the fiber material is generally in the range from about 0.015 to 1.0 wt-% and preferably from about 0.015 to 0.2 wt-%, based on the fiber material.

According to the present invention the amount of cyclodextrin derivative in the fiber material preferably is in the range from about 0.01 to 5.0 wt-%, more preferably from about 0.1 to 1.0 wt-%, based on the fiber material.

In another exemplary embodiment, the inventive fiber material additionally comprises cellulosic materials. Cellulosic materials are comprised of bonded, small discrete cellulosic fibers. Such fibers are typically held together by secondary bonds that, most probably, are hydrogen bonds. To form a cellulosic sheet, fiber is formed into a rough web or sheet on a fine screen from a water suspension or dispersion of fiber, combined with fiber additives, pigments, binder material, secondary binder materials or other components. Cellulosic materials can be made both from primary sources of fibers and from secondary or recycled fibrous materials.

According to an exemplary embodiment of the invention, a disposable hygiene or personal care article comprising the inventive fiber material is provided. In this, it is preferred that the article's top-sheet and/or absorbent layer incorporates the inventive fiber material in order to prevent or reduce the emission of malodors.

The cyclodextrin derivative (if used) is selected, based on the functional group compatibility with the polymer material of the fibers, the thermal stability of the cyclodextrin material and the cyclodextrin's ability to form an inclusion complex with volatile substances. The cyclodextrin derivative can contain one substituent on the single primary carbon hydroxyl and/or one substituent on one or both of the secondary carbon hydroxyls.

Cyclodextrin is commonly produced by a highly selective enzymatic synthesis. It generally consists of six, seven, or eight glucose monomers arranged in a donut shaped ring, which are denoted alpha-, beta-, or gamma-cyclodextrin, respectively. The specific coupling of the glucose monomers gives the cyclodextrin a rigid, truncated conical molecular structure with a hollow interior of a specific volume. This internal cavity is a key structural feature of the cyclodextrin, providing the ability to complex molecules (e.g., aromatics, alcohols, halides and hydrogen halides, carboxylic acids and their esters, etc.). The complexed molecule must satisfy the size criterion of fitting at least partially into the cyclodextrin internal cavity, resulting in an inclusion complex.

For use in the present invention, the cyclodextrin derivative may preferably based on alpha-cyclodextrin (alpha-CD), beta cyclodextrin (beta-CD), gamma-cyclodextrin (gamma-CD) or mixtures thereof. A preferred cyclodextrin derivative is, inter alia, selected based on the functional group compatibility with the fiber material on one hand and the cyclodextrin's ability to form an inclusion complex with targeted substances on the other hand.

Accordingly, a first requirement is compatibility with the thermoplastic material as well as thermal stability in the manufacturing process. "Compatible" means that preferably the cyclodextrin material can be uniformly dispersed into the fiber material, can retain the ability to trap or complex permeant materials or polymer impurity, and can reside in the polymer without substantial reductions in scavenging properties.

Second, the cyclodextrin's internal cavity size (i.e., α, β, γ) must be considered. Any derivative functional group modification must be suitable for forming an inclusion complex with targeted volatiles or impurities. To achieve a specific result, providing more than one cavity size and functional group may be necessary. For example, blends of α and/or β that contain γ-cyclodextrin have greater complexation efficiencies for some volatile substances than blends without γ-cyclodextrin. Computational modelling indicates that the type and number of functional groups on the ring provide different complexation energies for specific ligands (i.e., complexed substances). These complexation energies ($\Delta E^{steric}$ and $\Delta E^{electrostatic}$) can be calculated for a specific derivative, cavity size and ligand. Hence, inclusion complexation is predictable to some extent. For example, the inventors found out that acetylated α-cyclodextrin, acetylated β-cyclodextrin and acetylated γ-cyclodextrin are very effective cyclodextrin derivatives for improving the scavenging properties of the inventive fiber material.

The compatible cyclodextrin derivative according to the present invention is a compound substantially free of an inclusion complex. In this invention, the term "substantially free of an inclusion complex" means that the quantity of the dispersed cyclodextrin material in the fiber material contains a large fraction having cyclodextrin free of a contaminant, a permeant or other inclusion compound in the interior of the cyclodextrin molecule. A cyclodextrin compound is typically added and blended in the polymer without any inclusion compound but some complexing can occur during manufacture.

In principle, the preferred cyclodextrin derivative can contain one substituent on the single primary carbon hydroxyl and one substituent on one or both of the secondary carbon hydroxyls. Because of the geometry of the cyclodextrin molecule, and the chemistry of the ring substituents, the hydroxyl groups are not equal in reactivity. However, with care and effective reaction conditions, the cyclodextrin molecule can be reacted to obtain a derivatized molecule having a certain number of hydroxyl groups derivatized with a single substituent type. Further directed synthesis of a derivatized molecule with two different substituents or three different substituents is also possible. These substituents can be placed at random or directed to a specific hydroxyl. For the purposes of this invention, a broad range of pendant substituent moieties can be used on the molecule. These derivatized cyclodextrin molecules can include alkyl ether, silyl ether, alkyl ester, including cyclodextrin esters such as tosylates, mesylate and other related sulfo derivatives, hydrocarbyl-amino cyclodextrin, alkyl phosphono and alkyl phosphate cyclodextrin, imidazoyl substituted cyclodextrin, pyridine substituted cyclodextrin, hydrocarbyl sulphur containing functional group cyclodextrin, silicon-containing functional group substituted cyclodextrin, carbonate and carbonate substituted cyclodextrin, carboxylic acid and related substituted cyclodextrin and others.

Acyl groups that can be used as compatibilizing functional groups include acetyl, propionyl, butyryl, trifluoroacetyl, benzoyl and acryloyl groups. The formation of such groups on the hydroxyls of the cyclodextrin molecule involve well known reactions. The acylation reaction can be conducted using the appropriate acid anhydride, acid chloride, and well known synthetic protocols.

Cyclodextrin materials can also be reacted with alkylating agents to produced an alkylated cyclodextrin. Typical examples of alkyl groups useful in forming the alkylated cyclodextrin include methyl, propyl, benzyl, isopropyl, tertiary butyl, allyl, trityl, alkyl-benzyl and other common alkyl groups. Such alkyl groups can be made using conventional preparatory methods, such as reacting the hydroxyl group under appropriate conditions with an alkyl halide, or with an alkylating alkyl sulfate reactant.

Tosyl(4-methylbenzene sulfonyl), mesyl(methane sulfonyl) or other related alkyl or aryl sulfonyl forming reagents can also be used in manufacturing compatibilized cyclodextrin molecules.

Sulfonyl containing functional groups can be used to derivatize either of the secondary hydroxyl groups or the primary hydroxyl group of any of the glucose moieties in the cyclodextrin molecule. The reactions can be conducted using a sulfonyl chloride reactant that can effectively react with either primary and secondary hydroxyl. The sulfonyl chloride is used at appropriate mole ratios depending on the number of target hydroxyl groups in the molecule requiring substitution. Sulfonyl groups can be combined with acyl or alkyl groups.

The sulfonyl derivatized cyclodextrin molecule can be used to generate the amino derivative from the sulfonyl group substituted cyclodextrin molecule via nucleophilic displacement of the sulfonate group by an azide-ion. The azido derivatives are subsequently converted into substituted amino compounds by reduction. Large numbers of these azido or amino cyclodextrin derivatives have been manufactured. Examples of nitrogen containing groups that can be useful in the invention include acetylamino groups (—NHAc), alkylamino including methylamino, ethylamino, butylamino, isobutylamino, isopropylamino, hexylamino, and other alkylamino substituents. The amino or alkylamino substituents can further be reactive with other compounds that react with the nitrogen atom to further derivatize the amine group.

The cyclodextrin molecule also can be substituted with heterocyclic nuclei including pendent imidazole groups, histidine, imidazole groups, pyridino and substituted pyridino groups.

Cyclodextrin derivatives can be modified with sulfur containing functional groups to introduce compatibilizing substituents onto the cyclodextrin. Apart from the sulfonyl acylating groups mentioned above, sulfur containing groups manufactured based on sulfhydryl chemistry can be used to derivatize cyclodextrin. Such sulfur containing groups include methylthio (—SMe), propylthio (—SPr), t-butylthio (—S—$C(CH_3)_3$), hydroxyethylthio (—S—$CH_2$ $CH_2$ OH), imidazolylmethylthio, phenylthio, substituted phenylthio, aminoalkylthio and others. Based on the ether or thioether chemistry set forth above, cyclodextrin having substituents ending with a hydroxyl aldehyde ketone or carboxylic acid functionality can be prepared. Cyclodextrin with derivatives formed using silicone chemistry can contain compatibilizing functional groups.

Cyclodextrin derivatives with functional groups containing silicone, herein called silicon ether, can be prepared. Silicone groups generally refer to groups with a single substituted silicon atom or a repeating silicone-oxygen backbone with substituent groups. Typically, a significantly proportion of silicone atoms in the silicone substituent bear hydrocarbyl (alkyl or aryl) substituents. Silicone substituted materials generally have increased thermal and oxidative stability and chemical inertness. Further, the silicone groups increase resistance to weathering, add dielectric strength and improve surface tension. The molecular structure of the silicone group can be varied because the silicone group can have a single silicon atom or two to twenty silicon atoms in the silicone moiety, can be linear or branched, have a large number of repeating silicone-oxygen groups and can be further substituted with a variety of functional groups. For the purposes of this invention the simple silicone containing substituent moieties are preferred including trimethylsilyl, mixed methylphenyl silyl groups etc.

In exemplary embodiments of the present invention the cyclodextrin material comprises substituents having a silyl ether group, an alkyl ether group and/or an alkyl ester group. According to the present invention the alkyl ester substituents may comprise acetyl moieties, propyl moieties and/or butyl moieties and/or maleated polyethylene having a #$CH_2)_n$-chain wherein n=8 to 15,000, the alkyl ether substituents may comprise methyl moieties, ethyl moieties and/or propyl moieties and the silyl ether sub stituents may comprise methyl moieties, ethyl moieties, propyl moieties and/or butyl moieties.

The fiber material according to this invention can also contain other additives, which do not adversely affect the performance of the metal particles and/or the cyclodextrin. According to another exemplary embodiment, the inventive fibers or the resulting fiber material can additionally be treated (e.g. coated) with unmodified (or modified) cyclodextrin.

The modified cyclodextrin and/or the nanosized zinc or similar scavenging metal may preferably be dispersed in a thermoplastic fiber-building material. The resulting material can be a homogenous material with the scavenging actives substantially evenly dispersed throughout the polymer matrix. This homogenous material is formed into fibers by conventional methods as used in the industry. The manufacture of textiles or non-wovens from such fibers is also conventional.

In principle, the inventive fiber material can be obtained by a manufacturing method comprising the following steps:

a) physically mixing the particles of zinc or similar reacting metal or metal alloy and/or the cyclodextrin material into the material to be manufactured into fibers (fiber-building material), wherein the physically mixing may be achieved by extrusion, b) producing fibers from the material obtained in step a), preferably by melt spinning, wet spinning, electrospinning or dry spinning.

If the fiber material is a synthetic thermoplastic material, the inventive fiber material comprising at least one thermoplastic polymer, a nanosized zinc or similar scavenging metal and a modified cyclodextrin can be created e.g. by the following procedure:

In a first (optional) step a cyclodextrin-containing thermoplastic material is prepared by physically mixing and dispersing the minor constituent, i.e. modified cyclodextrin into the major constituent, i.e. the polymer, e.g. by extrusion. Suitable extrusion techniques include the so-called "direct incorporation" and "masterbatch addition". In either method it is preferred to use twin-screw co-rotating segmented barrel extruders. Of course it is also possible to use counter rotating or single screw extruders for mixing or dispersing the cyclodextrin material into the polymeric material. It is clear that the modified cyclodextrin can be added individually or in combination with other suitable additives or adjuvants.

After mixing or dispersing the cyclodextrin material into the polymeric material the nanosized zinc particles are dispersed in the resulting molten plastic. The reactive zinc particles to be added usually are dispersed in a mineral oil to protect the zinc from oxygen and moisture. At least some portion of mineral oil is stripped from the plastic e.g. in the extruder using heat and vacuum. The resulting material is e.g. pumped out of the extruder and pelletized.

Alternatively, the metal particles can be dry blended with the polymeric material or polymeric powder.

However, it is also possible to add the zinc or metal particles to the polymer material and subsequently add the cyclodextrin material in order to obtain fiber materials according to the present invention.

The material comprising the polymer and the scavenging actives is then subjected to conventional processing for the manufacture of textile fibers or non-woven fibers. It may be advantageous to produce fibers by using spunbond processes or meltblowing processes.

Such fibers may then be processed into textiles or nonwovens and may be used to manufacture top-sheets, absorptive layers and other components of hygiene and personal care articles with improved olfactory performance in and after use.

The foregoing discussion illustrates various embodiments of the invention. The following examples and data further exemplify the invention.

Nano-size Zinc and Triacetyl Alpha-Cyclodextrin Masterbatch Compounding

A segmented barrel (seven barrels), co-rotating compounding extruder (Haake 16 mm twin screw with a 28:1 L/D) was configured with an up-stream feed zone for homopolymer polypropylene (ExxonMobil PP3155 for non-woven fiber applications) having a 0.9 g/cm3 density and a melt flow rate (230° C./2.16 Kg) of 36 g/10 min. A weight loss feeder is used to deliver PP into the barrel. The polypropylene was starve fed into the first zone, melted in the second zone using 60° offset mixing elements followed by 90° offset mixing elements and a reverse half feed screw. In the third zone, the zinc suspension (1 part zinc to 2 parts oil wt./wt.) was fed through a port in the top of the extruder using a low injection rate pump (Ministatic Pump manufactured by Manostatic). During processing, the zinc/oil suspension was constantly agitated using a stir plate and stir bar. The zinc mixture (pumped at 63.6 grams Zn/hr) containing 0.467 grams Zn/milliliter of mineral oil. In the fourth zone, the zinc was mixed into polypropylene using the same mixing elements as in the second zone. The fifth zone consisted of conveying screw elements to pump the resin through the die. The feed rate of the resin was 2 kg per hour, all zone temperatures were set at 150° C., the rpm of the screws were 130, the melt temperature at the die was 230° C. and the torque was 60-75% of maximum. The strands pass through a water bath and two air wipes before entering the strand cutter. The finished pellets are placed into a nitrogen purged Mylar/foil composite bag heat sealed with a bag sealer to prevent atmospheric contamination until use.

The 3.2 wt.-% Haake nanozinc masterbatch above was further let down to a 0.35% nano zinc masterbatch using a one (1) inch Killion single screw extruder. The 3.2 wt.-% nanozinc masterbatch was dry pre-blended with virgin PP3153 and the blend fed into the feed zone using a volumetric feeder. The finished pellets are placed into a nitrogen purged Mylar/foil composite bag heat sealed with a bag sealer to prevent atmospheric contamination until use.

An alternative manufacturing procedure for producing a nanozinc masterbatch is dry pre-blending the nanozinc with polypropylene powder (20 to 500 micron particle size). The nanozinc powder is added to the PP micro-powder at a 0.25 wt-% to 1.0 wt.-%. The PP micro-powder is used as a binding agent for the nanozinc. Standard dry-blending equipment (ribbon blenders, fluidized action mixers, V-shell blenders and cone mixers) is used to homogenize the polymer and nanozinc prior to extrusion compounding. The PP/nanozinc powder mixture is fed directly into the throat of the extruder using a volumetric or weight loss feeder.

A second masterbatch formulation was produced with triacetyl alpha cyclodextrin without zinc. The triacetyl alpha cyclodextrin was dried at 105° C. for 12 hours. The 5% triacetyl alpha cyclodextrin in PP3155 was produced using a 16 mm Haake twin screw extruder with a 28:1 L/D and the same screw configuration and conditions as the zinc masterbatch. The PP3155 and triacetyl alpha cyclodextrin were dry blended and fed into the port in zone 1, and the port in zone 3 was closed. The strands pass through a water bath and two air wipes before entering the strand cutter. The finished pellets are placed into a nitrogen purged Mylar/foil composite bag and heat-sealed.

Masterbatch formulation #1 contained 99.65% PP3155 and 0.35% nano-size particle zinc (80-100 nm). Masterbatch formulation #2 contained 95.0% PP3155 and 5% triacetyl alpha cyclodextrin. The nanozinc material was obtained from Argonide, the heavy mineral oil from Aldrich Chemical and triacetyl alpha cyclodextrin was manufactured by Wacker Biochem Corporation.

TABLE 1

PP3155 masterbatch formulations.

| Masterbatch Formulations | Masterbatch Compositions (wt.-% in PP3155) | |
| --- | --- | --- |
| | Nanozinc Particle size 80-100 nm | Triacetyl α CD Degree of Substitution = 3.0 |
| Formulation #1 | 0.35 wt.-% | |
| Formulation #2 | | 5 wt.-% |

Nonwoven Fiber Mat Preparation

A series of nonwoven fiber materials using virgin PP3155 and the two masterbatch formulations in Table 1 were converted into nonwoven fiber mat (Table 2) using a spunbound manufacturing process. The nonwoven fiber mat was produced on a 1 meter Reicofil II Spunbond Line. Weight loss feeders were used to deliver PP3155 virgin pellets and masterbatch pellets into the extruder feed zone based on the weight percents in Table 2. The target of 22 μm fibers in 25 gm/m² mats were produced and confirmed on each formula. All formulations were produced under the same process conditions and no measurable differences were observed in the process measurements. Fiber diameter is an average of 10 measurements with the exception of Mat #4 where 20 measurements were taken. The diameter of non zinc fiber (control PP and cyclodextrin containing fiber) is 22.0 μm, and the zinc containing fiber is 21.4 μm.

TABLE 2

Spunbound nonwoven fiber mat test samples.

| Nonwoven Fiber Mat samples | Masterbatch Formulations | Nonwoven Fiber Compositions [% by wt.] | | |
| --- | --- | --- | --- | --- |
| | | PP3155 | Nanozinc | Triactyl α Cyclodextrin |
| Mat #1 | | 100% | | |
| Mat #2 | Formulation #1 | 99.965% | 0.035% | |
| Mat #3 | Formulation #2 | 99.5% | | 0.50% |
| Mat #4 | Formulation #1 | 99.95% | 0.050% | |
| Mat #5 | Formulation #'s 1&2 | 99.465 | 0.035% | 0.50% |

Organic Vapor Sorption. The term sorption is generally used to describe the initial penetration and dispersal of permeant molecules into a polymer matrix and includes both adsorption and absorption as well as cluster formation. Sorption behavior is based on the relative strengths of the interactions between the permeant molecules and the polymer, or between the permeant molecules themselves within the polymer, or immobilization of permeant molecules by sites (e.g., zinc and cyclodextrin) in the polymer. The sorption test method is most easily explained in terms of a nonwoven fiber mat structure surrounded by a fixed volume (e.g., glass jar). The fiber mat structure and the volume are initially completely free of the test solute inside the close-volume jar. At time zero, and at several subsequent times, the test mats are exposed to a known concentration of test solute. The headspace concentration in the fixed volume surrounding the test structure is quantitated using gas chromatography. The sorptive rate and capacity of the nonwoven structure is determined from the headspace concentration in the closed vessel. The effectiveness of the fiber for reducing the solute headspace concentration is directly related to fiber sorption.

This experimental technique is designed to quantitatively measure solute headspace concentration in the fixed-volume cell. High-resolution gas chromatography (HRGC) operated with electron capture detection (ECD) is used to measure the headspace concentration. The solute in the headspace is quantitatively collected by solid phase microextraction (SPME) from the test cell and analyzed by HRGC/ECD. Solute concentration is determined from calibration standards and measured in micrograms (μg).

Instrument Conditions. The following SPME HRGC/ECD instrument conditions used in the analyses are provided in Table 3.

TABLE 3

Method condition for gas chromatograph and solid phase microextraction.

| Method: | Chloroacetic acid |
| --- | --- |
| Target permeants: | Chloroacetic acid |
| Sampling technique: | Solid Phase Microextraction (SPME) |
| Fiber: | Carbowax/Divinylbenzene (70 mm) |
| Sorb time: | 2 minutes at room temperature |
| Desorb time: | 1 minute at 220° C. |
| Column: | Retention gap |
| Dimensions: | 3M × 0.25 mm i.d. |
| Film thickness: | Uncoated |
| Carrier gas: | Helium |
| Headpressure: | 8 psi (0.35 mL/min) |
| Injection mode: | Splitless |
| Detector: | Electron Capture (ECD) |
| Detector temp: | 290° C. (60 mL/min Nitrogen) |
| Injector temp: | 220° C. |
| Initial temp: | 50° C. |
| Initial hold: | 3 minutes |
| Temperature rate: | 0° C./minute |
| Final temperature: | 50° C. |
| Final hold: | |
| Total analysis time: | 3 minutes |

Nonwoven fiber mat samples (mat cut into a 12.7 cm×12.7 cm square having 22 μm fibers in a 25 gm/m² mat) are tested in a closed-volume vapor sorption cell (refer to FIG. 1). The closed-volume cell method has two glass compartments (i.e., cells). The large cell side has a volume of 1,200-mL and the small side cell a volume of 280-mL. Two test mats are placed inside the large cell side; the cells are assembled using soft, aluminum sealing rings to provide a hermetic seal between the glass cells as screws around the sealing flange firmly pull the two cells together forming the air tight seal. The sorption standard for evaluating the nonwoven test mats contains chloroacetic acid. The physical and chemical parameters of chloroacetic acid are provided in Table 4.

Example 1

Quantitative Sorption Performance of Nonwoven Mat

Figure 2:
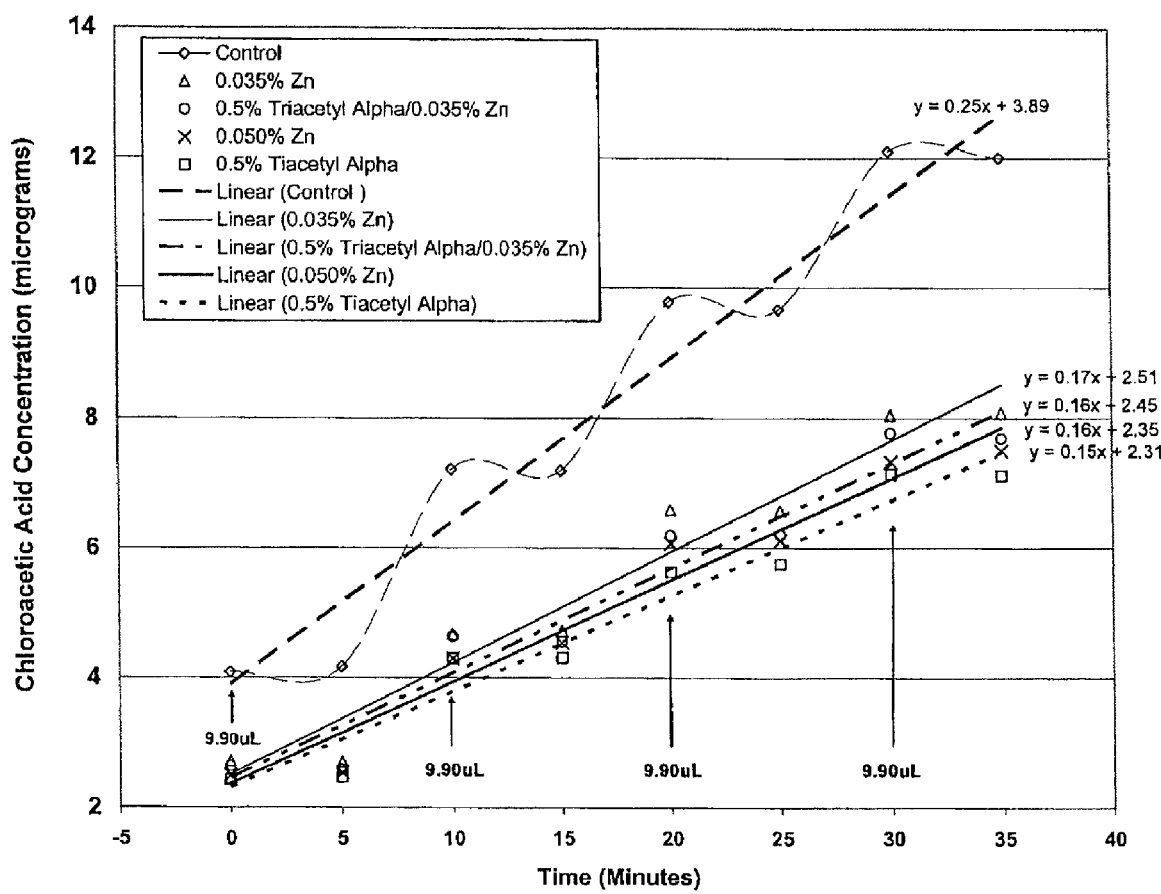
FIG. 2 Chloroacetic acid sorption profiles of five fiber mats. Headspace concentration of chloroacetic acid (in µg) as a function of time for jars containing mat compositions containing nanozinc and/or cyclodextrin. Four sequential additions of 9.90 µg each of chloroacetic acid was added to sealed glass jars containing nonwoven mats at time=0, 10, 20 and 30 minutes.

Nonwoven mat reactivity and capacity was measured by placing test mats into a glass jar which is subsequently sealed and then filled with a reactive test vapor. Over the test time period, the headspace vapor partitions into the fiber. The vapor concentration is measured in the headspace of the glass jar as a function of time. These data are used to quantitatively measure the sorptive performance of these active nonwoven mats. The measured effect of the active zinc and/or cyclodextrin in the fiber matrix is a reduction in the vapor concentration in the jar compared to PP fiber without the active technology. The partition coefficient and diffusion coefficient will be identical for test mats since the PP polymer is identical. The headspace concentration over the test period (40 min) demonstrates the effectiveness of the test mats for removing volatile molecules from the headspace. Nonwoven test mat performance is then a function of the sorption of chloroacetic acid in the nonwoven mat fiber resulting in a corresponding decrease in the headspace. Four sequential 1-μl injections of chloroacetic acid dissolved in methanol (at 9.90 μg chloroacetic acid/μL) were made into the glass jar through a rubber septum. The first chloroacetic acid injection is at time zero, then three additional injections were made at 10, 20 and 30 minutes, respectively. The headspace was measured by taking a time composite sample every five minutes after the chloroacetic acid injection using a two minute SPME sampling interval. The SPME headspace samples are analyzed by HRGC/ECD (method conditions Table 3). Quantitative results are provided in Table 5 and plotted in FIG. 2.

TABLE 4

Chloroacetic acid physical and chemical test permeant parameters.

| Permeant | Molecular Weight | Boiling Point [° C.] | Diffusion[1] D, [m²/sec] | Dissociation Constants in Aqueous Solutions | | |
| --- | --- | --- | --- | --- | --- | --- |
| | | | | K | pK | Temp. [° C.] |
| Chloroacetic acid | 94.50 | 189 | $6.98 \times 10^{-13}$ | $1.40 \times 10^{-3}$ | 2.85 | 25 |

[1]Calculated by lag time in HDPE blown film.

TABLE 5

Headspace concentration of chloroacetic acid (in μg) as a function of time for jars containing mat compositions containing nanozinc and/or cyclodextrin. Four sequential additions of 9.90 μg each of chloroacetic acid was added to sealed glass jars containing nonwoven mats at time = 0, 10, 20 and 30 minutes.
Chloroacetic Acid Jar Headspace Concentration
(Headspace concentration in micrograms - μg)

| | Chloroacetic acid Additions | | | | | | | | |
|---|---|---|---|---|---|---|---|---|---|
| | Inj. | | Inj. | | Inj. | | Inj. | | |
| | Elapsed Time (min) | | | | | | | | |
| Sample Conc. | 0 μg | 5 μg | 10 μg | 15 μg | 20 μg | 25 μg | 30 μg | 35 μg | 40 μg |
| Mat #1 (Control) | 4.09 | 4.16 | 7.21 | 7.19 | 9.78 | 9.67 | 12.1 | 12.0 | 11.3 |
| Mat #2 (0.035-% nano Zn) | 2.71 | 2.70 | 4.66 | 4.71 | 6.59 | 6.57 | 8.05 | 8.08 | 7.95 |
| Mat #3 (0.5% TA-α-CD) | 2.43 | 2.46 | 4.29 | 4.30 | 5.63 | 5.75 | 7.13 | 7.12 | 7.05 |
| Mat #4 (0.05% nano Zn) | 2.49 | 2.53 | 4.29 | 4.53 | 6.07 | 6.11 | 7.33 | 7.50 | 7.47 |
| Mat #5 (0.5% TA-α-CD + 0.035% nano Zn) | 2.63 | 2.58 | 4.63 | 4.54 | 6.19 | 6.20 | 7.77 | 7.69 | 7.51 |

This experiment provides the functional capacity estimates for the nanozinc and/or cyclodextrin containing nonwoven fiber. A least squares linear regression fit to the chloroacetic acid headspace concentrations as a function of time show a 0.251 μg/min. slope for control mat and 0.171, 0.161, 0.157 and 0.147 μg/min. for 0.035 wt.-% nanozinc, 0.05 wt.-% nanozinc, 0.5 wt.-% triacetyl α cyclodextrin+0.035 wt.-% nanozinc and 0.5 wt.-% triacetyl α cyclodextrin, respectively. The chloroacetic acid concentration slope is 1.7 times greater for the control nonwoven mat than 0.5 wt.-% triacetyl a cyclodextrin nonwoven mat over the time-period from 0 minutes to 40 minutes. Similar slope concentration differences were measured for the other nonwoven mat samples containing nanozinc and cyclodextrin/nanozinc combinations. The nonwoven fiber examples in Table 5 clearly demonstrate PP fiber containing adsorptive sites (nanozinc and/or cyclodextrin), sorb and immobilize more headspace solute molecules than PP fiber without adsorptive or reactive sites. The effect of a faster solute sorption rate is to reduce the concentration of malodor compounds in air surrounding the fiber.

Example 2

Sensory Evaluation of Nonwoven Mat for Malodor Reduction

A synthetic diaper malodor concentrate (produced by Bush Boake Allen, Ltd.) was used to evaluate the odor reducing performance in the nonwoven mats in Table 2. Analysis of the "neat" malodor concentrate by gas chromatography mass spectrometry indicated approximately fifteen major compounds (Table 6). The general classes of chemicals contained in the synthetic malodor are organic acids, sulfur, nitrogen and aromatic alcohol compounds. Most of the compounds identified in Table 6 have human sensory thresholds in the low parts per billion, and for one compound, 3-methylindole (skatole), a threshold in the low parts per trillion. Skatole is a common fecal odor. Research literature on volatile malodor-causing substances in human waste (feces and urine) show about 90% of the malodor causing substances were fatty acids: acetic acid, propanoic acid, and butyric acid. Ammonia is listed at about 6.5%. Other malodor-causing minor substances were skatole, indole, pyrine, pyrrole, hydrogen sulfide and methyl mercaptan.

TABLE 6

Compounds identified in synthetic malodor by gas chromatography mass spectrometry.

| Organic Acids | Sulfur | Nitrogen | Aromatic Alcohol |
|---|---|---|---|
| Acetic acid | Carbon disulfide | Ammonia | 4-Methylphenol |
| Butyric acid | Mercaptoacetic acid | 4-Methylmorpholine | |
| Isovaleric acid | 2-Naphthalenethiole | 4-Methyl-4-oxide morpholine | |
| Hexanoic acid | | Dimethylhydantoin | |
| Octanoic acid | | 3-Methylindole | |
| | | Hexanamide | |

Detection of the synthetic diaper malodor compounds in the standard static sorption test at concentrations that represent real world unpleasant sensory values is not feasible because the human sensory threshold for these compounds is well below the detection limits of these compounds by instrumental methods of analysis. While gas chromatography equipped with various detectors will give specific qualitative and quantitative measurements on malodor components, odor perception is based on the component stream, not just individual components. The instrumental analytical techniques were abandoned and sensory techniques (i.e., human nose) were substituted for odor intensity detection.

Figure 3:
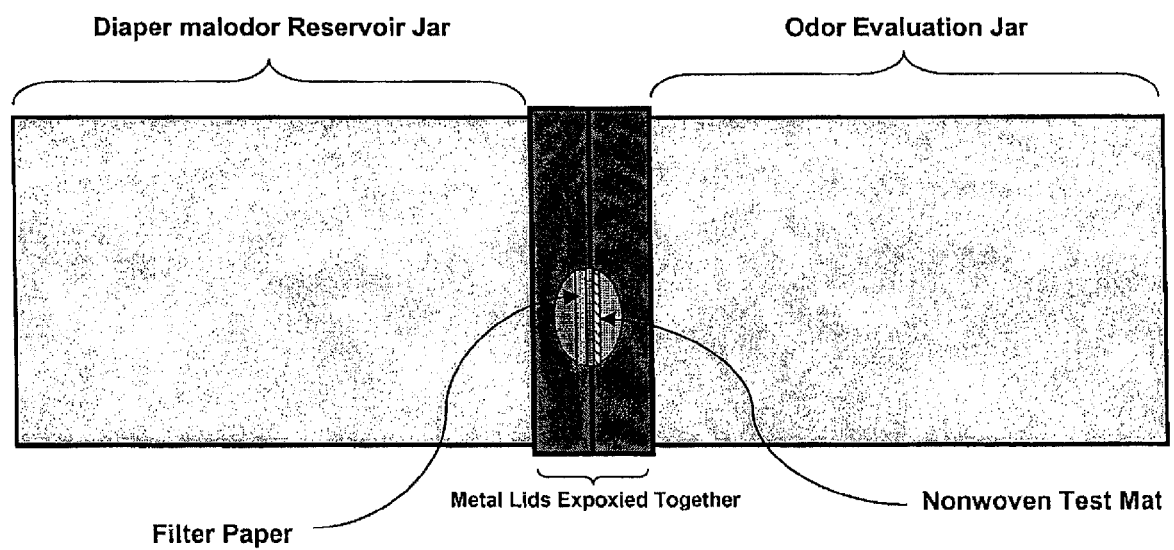
FIG. 3 Closed-volume static permeation cells for malodor vapor permeation sensory testing.

Experimental mat diaper malodor reduction performance was measured in static permeation cells constructed from Mason brand glass canning jars. Each jar has a volume of approximately 450-ml. Two screw cap lids are attached top-to-top with epoxy adhesive allowing the two jars to be attached as shown in FIG. 3. One of the jars serves as a reservoir for the diaper malodor and attachment of the mat by stretching the mat over the jar mouth and screwing the lid over the mat. Immediately under the mat is an absorbent filter paper cut to the diameter and used to release the diaper malodor standard during testing The other jar serves as a collection reservoir for the permeating malodor compounds. This jar is screwed to the opposing lid and is removed periodically during the test to evaluate odor. Teflon tape is used on the glass jar threads prior to assembly to securely seal the jars during the test.

The diaper malodor concentrate was diluted 1,100× and 715× in deionized water. An aliquot of the malodor dilution is transferred to a filter paper cone in the malodor reservoir side. Next, the test mat is placed over the open end of the jar with approximately 2-cm of mat extending beyond the jar's lip. Then the double-sided cap is screwed down tightly followed by the odor evaluation jar. One (1) milliliters of the dilution correspond to a mass of active malodor compounds of approximately 200 µg for the 1,100× dilution and approximately 315 µg for the 715× dilution. The mass of active malodor compounds injected is greater than the capacity of the test mat used in the method. The odor evaluation jars were maintained at 38° C. Deionized water dilutions of the malodor provided water vapor in the malodor reservoir side to simulate the environment of a used diaper. The odor evaluation jar is unscrewed and evaluated for odor and quickly replaced. Generally, two (2) odor evaluations are made over the test period for malodor intensity. An eight-point malodor intensity scale from 0=no malodor to 8=very strong malodor was used. Randomized test samples are provided to the panelist who independently ranks the malodor intensity. Samples yielding an odor ranking below about 2 would barely be perceived by the general public.

TABLE 7

Sensory malodor intensity scores for nonwoven Mat #1 (control) and four active nonwoven fiber mats. Tests were conducted with approximately 200 µg of active malodor compounds. Odor evaluation jars were maintained at 38° C. during testing.

Nonwoven Fiber Mat Malodor Sensory Score*
(Test mat: 12.7 cm × 12.7 cm square, 22 µm fibers in a 25 gm/m² mat)

| Time (min.) | Mat #1 (control) | Mat #2 (0.035% Zn) | Mat #3 (0.5% TA-α-CD) | Mat #4 (0.05% Zn) | Mat #5 (0.5% TA-α-CD + 0.035% Zn) |
|---|---|---|---|---|---|
| 75 | 4 | 2 | 1 | 1 | 1 |
| 125 | 4 | 2 | 0 | 1 | 1 |

Key:

0 = No odor;

1 = Just detectable odor;

2 = Very slight odor;

3 = Slight odor;

4 = Slight-Moderate odor;

5 = Moderate odor;

6 = Moderate-Strong odor;

7 = Strong odor;

8 = Very strong odor

TABLE 8

Sensory malodor intensity scores for nonwoven Mat #1 (control) and four active nonwoven fiber mats. Tests were conducted with approximately 315 µg of active malodor compounds. Odor evaluation jars were maintained at 38° C. during testing.

Nonwoven Fiber Mat Malodor Sensory Score*
(Test mat: 12.7 cm × 12.7 cm square, 22 µm fibers in a 25 gm/m² mat)

| Time (min.) | Mat #1 (control) | Mat #2 (0.035% Zn) | Mat #3 (0.5% TA-α-CD) | Mat #4 (0.05% Zn) | Mat #5 (0.5% TA-α-CD + 0.035% Zn) |
|---|---|---|---|---|---|
| 60 | 5 | 4 | 3 | 3 | 2 |

Key:
0 = No odor;
1 = Just detectable odor;
2 = Very slight odor;
3 = Slight odor;
4 = Slight-Moderate odor;
5 = Moderate odor;
6 = Moderate-Strong odor;
7 = Strong odor;
8 = Very strong odor The tests results in Tables 7 and 8 show a significant odor intensity improvement for active fiber Mat #2 through Mat #5 over Mat #1 (control) for the malodor test concentrations and odor evaluation times. The combination of a nanozinc and triacetyl alpha cyclodextrin show better malodor reduction for the synthetic diaper malodor concentrate than cyclodextrin or nanozinc alone. However, also the incorporation of nanozinc or triacetyl alpha cyclodextrin leads to a significant malodor reduction for the synthetic diaper malodor concentrate. The effectiveness of the active nonwoven fibers is clearly been demonstrated in terms of kinetic rate of reduction as established in the quantitative closed-volume sorption test and also in human odor perception based on a complex synthetic mixture of malodor components.

The invention claimed is:

1. A fiber material having improved malodor scavenging properties, comprising:

(a) fibers; and (b) dispersed within the fibers, an effective malodor scavenging amount of a cyclodextrin material; wherein the cyclodextrin is free of an inclusion complex compound and the cyclodextrin comprises one of an α-cyclodextrin, a β-cyclodextrin, a γ-cyclodextrin and mixtures thereof, having one of pendant moieties and substituents that render the cyclodextrin compatible with the fiber material, wherein the fibers are made by electrospinning a polymer solution containing the malodor scavenging amount of the cyclodextrin, the cyclodextrin comprising at least one substituent having an alkyl ether group.

2. The material of claim 1, wherein the fiber material is a thermoplastic material.

3. The material of claim 2, wherein the thermoplastic material is selected from the group consisting of polyolefines, polyester, polyamides, acrylic polymers, cellulosic polymers, polycarbonates, polyimide materials, polyvinyl alcohol, polysulfone, polyphenylene sulfide, polyphenylene oxide, polystyrene, polystyrene copolymers, polyvinyl chloride, polyvinylidene chloride, polyether ketones and mixtures thereof.

4. The material of claim 2, wherein the thermoplastic material is a polypropylene.

5. The material of claim 1, wherein the amount of cyclodextrin material in the fiber material is in the range from about 0.01 to 5 wt.-% based on the fiber material.

6. The material of claim 1, wherein the substituents having the alkyl ether group comprise at least one moiety selected from the group consisting of methyl moieties, ethyl moieties and propyl moieties.

7. The material of claim 1, wherein the particles of the cyclodextrin material are uniformly dispersed in the fibers.

8. A method for manufacturing a fiber material having improved malodor scavenging properties, comprising:
   (a) physically forming a polymer solution containing a cyclodextrin material, the cyclodextrin being free of an inclusion complex compound and the cyclodextrin comprising one of an α-cyclodextrin, a β-cyclodextrin, a γ-cyclodextrin and mixtures thereof, having one of pendant moieties and substituents that render the cyclodextrin compatible with the fiber material
   (b) producing fibers by electrospinning the polymer solution containing the malodor scavenging amount of the cyclodextrin, the cyclodextrin comprising at least one substituent having an alkyl ether group.

9. A hygienic article, comprising:
   a fiber material having improved malodor scavenging properties, the fiber material comprising fibers and, dispersed within the fibers, an effective malodor scavenging amount of a cyclodextrin material,
   wherein the cyclodextrin is free of an inclusion complex compound and the cyclodextrin comprises one of an α-cyclodextrin, a β-cyclodextrin, a γ-cyclodextrin and mixtures thereof, having one of pendant moieties and substituents that render the cyclodextrin compatible with the fiber material, wherein the fibers are made by electrospinning a polymer solution containing the malodor scavenging amount of the cyclodextrin, the cyclodextrin comprising at least one substituent having an alkyl ether group.

10. The hygienic article of claim 9, wherein the article is a disposable diaper.

11. The hygienic article of claim 10, wherein at least one of a facing layer and an absorbent layer of the disposable diaper comprises the fiber material having improved malodor scavenging properties.

* * * * *